US009624207B2

(12) United States Patent
Parthasaradhi Reddy et al.

(10) Patent No.: US 9,624,207 B2
(45) Date of Patent: Apr. 18, 2017

(54) POLYMORPHS OF AZILSARTAN MEDOXOMIL

(71) Applicant: HETERO RESEARCH FOUNDATION, Hyderabad Andhra Pradesh (IN)

(72) Inventors: Bandi Parthasaradhi Reddy, Hyderabad (IN); Kura Rathnakar Reddy, Hyderabad (IN); Dasari Muralidhara Reddy, Hyderabad (IN); Matta Ramakrishna Reddy, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 162 days.

(21) Appl. No.: 14/416,324

(22) PCT Filed: Jul. 19, 2013

(86) PCT No.: PCT/IN2013/000450
§ 371 (c)(1),
(2) Date: Jan. 22, 2015

(87) PCT Pub. No.: WO2014/033740
PCT Pub. Date: Mar. 6, 2014

(65) Prior Publication Data
US 2015/0183767 A1 Jul. 2, 2015

(30) Foreign Application Priority Data

Aug. 27, 2012 (IN) .......................... 3515/CHE/2012

(51) Int. Cl.
*C07D 413/10* (2006.01)
*C07D 413/14* (2006.01)
(Continued)

(52) U.S. Cl.
CPC ........ *C07D 413/10* (2013.01); *A61K 31/4245* (2013.01); *B01F 3/0807* (2013.01);
(Continued)

(58) Field of Classification Search
CPC ................................................... C07D 413/10
See application file for complete search history.

(56) References Cited

U.S. PATENT DOCUMENTS

2005/0187269 A1    8/2005  Kuroita et al.

FOREIGN PATENT DOCUMENTS

| IN | WO 2012090043 A1 * | 7/2012 | .......... C07D 413/14 |
| WO | 2012090043 A1 | 7/2012 | |
| WO | 2012107814 A1 | 8/2012 | |

OTHER PUBLICATIONS

International Search Report dated Jan. 31, 2014.

* cited by examiner

*Primary Examiner* — Matthew Coughlin
(74) *Attorney, Agent, or Firm* — Caesar Rivise, PC

(57) ABSTRACT

The present invention provides a novel amorphous Form of azilsartan acid, process for its preparation and pharmaceutical compositions comprising it. The present invention also provides novel crystalline Forms of azilsartan medoxomil, processes for their preparations and pharmaceutical compositions comprising them. The present invention further provides a novel amorphous Form of azilsartan medoxomil potassium, process for its preparation and pharmaceutical compositions comprising it. The present invention further provides a novel process for the preparation of azilsartan medoxomil potassium crystalline Form II.

21 Claims, 6 Drawing Sheets

(51) Int. Cl.
*A61K 31/4245* (2006.01)
*B01F 3/08* (2006.01)
*B01F 11/00* (2006.01)
*B01F 15/00* (2006.01)
*B01F 15/02* (2006.01)
*C12M 1/33* (2006.01)
*G01N 1/38* (2006.01)

(52) U.S. Cl.
CPC .... *B01F 11/0028* (2013.01); *B01F 15/00331* (2013.01); *B01F 15/00389* (2013.01); *B01F 15/00396* (2013.01); *B01F 15/00538* (2013.01); *B01F 15/026* (2013.01); *C07D 413/14* (2013.01); *C12M 45/02* (2013.01); *G01N 1/38* (2013.01); *B01F 2215/0073* (2013.01); *C07B 2200/13* (2013.01)

POLYMORPHS OF AZILSARTAN MEDOXOMIL

This application is a National Stage application of PCT/IN/2013/000450 filed 07/19/2013, which claims the benefit of Indian Provisional Patent Application No. 3515/CHE/2012, filed on Aug. 27, 2012, which are incorporated herein by reference.

FIELD OF THE INVENTION

The present invention provides a novel amorphous Form of azilsartan acid, process for its preparation and pharmaceutical compositions comprising it. The present invention also provides novel crystalline Forms of azilsartan medoxomil, processes for their preparations and pharmaceutical compositions comprising them. The present invention further provides a novel amorphous Form of azilsartan medoxomil potassium, process for its preparation and pharmaceutical compositions comprising it. The present invention further provides a novel process for the preparation of azilsartan medoxomil potassium crystalline Form II.

BACKGROUND OF THE INVENTION

Azilsartan medoxomil is chemically, (5-methyl-2-oxo-1,3-dioxol-4-yl)methyl-2-ethoxy-1-([2'-(5-oxo-4,5-dihydro-1,2,4-oxadiazol-3-yl)biphenyl-4-yl]methyl)-1H-benzimidazole-7-carboxylate and has the structural formula:

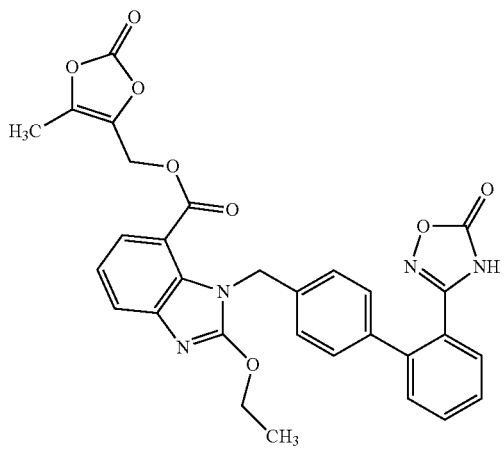 [SMILES: CCOc1nc2cccc(C(=O)OCc3oc(=O)oc3C)c2n1Cc1ccc(-c2ccccc2-c2noc(=O)[nH]2)cc1]

Azilsartan (INN, codenamed TAK-536) is an angiotensin II receptor antagonist used in the treatment of hypertension. It is marketed by Takeda Pharmaceuticals under the brand name EDARBI®.

Azilsartan acid and its process were disclosed in U.S. Pat. No. 5,243,054 (054 patent).

Azilsartan medoxomil and its potassium salt were disclosed in U.S. Pat. No. 7,157,584 (584 patent).

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Solvent medium and mode of crystallization play very important role in obtaining one polymorphic Form over the other.

Azilsartan medoxomil and its potassium salt can exist in different polymorphic Forms, which may differ from each other in terms of stability, physical properties, spectral data and methods of preparation.

Process for the preparation of azilsartan medoxomil was disclosed in the '584 patent. According to the patent, crystalline solid of azilsartan medoxomil was obtained by reacting 2-ethoxy-1-{[2'-(5-oxo-4,5-dihydro-1,2,4-oxadiazol-3-yl)biphenyl-4-yl]methyl}-1H-benzimidazole-7-carboxylic acid with 4-hydroxymethyl-5-methyl-1,3-dioxol-2-one in N,N-dimethylacetamide in the presence of p-toluenesulfonyl chloride, N,N-dimethylaminopyridine and potassium carbonate at low temperature to give solvate. The obtained solvate was crystallized in water and acetone to obtain azilsartan medoxomil. The crystalline azilsartan medoxomil obtained by the process of the prior art is herein after designated as azilsartan medoxomil crystalline Form I. The powdered x-ray diffractogram (PXRD) of azilsartan medoxomil crystalline Form I is shown in FIG. 2. Crystalline Form I of azilsartan medoxomil is characterized by peaks in the powder x-ray diffraction spectrum having 2θ angle positions at about 11.6, 13.3, 16.0, 20.3, 23.3, 23.5 and 24.1±0.2 degrees.

International patent application publication no. WO 2012/090043 disclosed crystalline Form $J_2$, $J_3$, $J_4$, $J_5$, $J_6$, $J_7$, $J_8$, $J_9$ and amorphous Form of azilsartan medoxomil.

An unpublished application, IN 2760/CHE/2012 assigned to Hetero Research Foundation discloses a crystalline Form II of azilsartan medoxomil potassium. The application also disclosed a crystalline Form II of azilsartan acid.

We have found a novel amorphous Form of azilsartan acid. The novel crystalline Form of azilsartan acid is stable, reproducible and so, suitable for pharmaceutical preparations.

We have also found novel crystalline Forms of azilsartan medoxomil. The novel crystalline Forms of azilsartan medoxomil are stable, reproducible and so, suitable for pharmaceutical preparations.

We have also found a novel amorphous Form of azilsartan medoxomil potassium. The novel amorphous Form of azilsartan medoxomil potassium is stable, reproducible and so, suitable for pharmaceutical preparations.

We have also found a novel process for the preparation of azilsartan medoxomil potassium crystalline Form II.

Thus, one object of the present invention is to provide a novel amorphous Form of azilsartan acid, process for its preparation and pharmaceutical compositions comprising it.

Another object of the present invention is to provide novel crystalline Forms of azilsartan medoxomil, processes for their preparation and pharmaceutical compositions comprising them.

Another object of the present invention is to provide a novel amorphous Form of azilsartan medoxomil potassium, process for its preparation and pharmaceutical compositions comprising it.

Another object of the present invention is to provide a novel process for the preparation of azilsartan medoxomil crystalline Form II.

SUMMARY OF THE INVENTION

In one aspect, the present invention provides an amorphous Form of azilsartan acid.

In another aspect, the present invention provides a process for the preparation of azilsartan acid amorphous Form, which comprises:
  a) providing a solution of azilsartan acid in a solvent; and
  b) removing the solvent from the solution to obtain azilsartan acid amorphous Form.

In another aspect, the present invention provides a pharmaceutical composition comprising amorphous Form of azilsartan acid and pharmaceutically acceptable excipients.

In another aspect, the present invention provides a crystalline Form of azilsartan medoxomil designated as Form H1 characterized by peaks in the powder x-ray diffraction spectrum having 2θ angle positions at about 4.4, 9.3, 10.6, 12.4, 16.8, 17.9, 18.1, 19.0, 19.9, 22.2, 22.8, 23.1 and 23.7±0.2 degrees.

In another aspect, the present invention provides a process for the preparation of azilsartan medoxomil crystalline Form H1, which comprises:
  a) reacting azilsartan acid in dimethylacetamide with 4-hydroxymethyl-5-methtyl-1,3-dioxol-2-one at below 5° C.;
  b) adding p-toluenesulfonyl chloride, N,N-dimethylaminopyridine and potassium carbonate to the reaction mass obtained in step (a) at below 5° C.;
  c) removing the solvent to obtain a residual mass;
  d) adding an ester solvent and water to the residual mass;
  e) pH of the reaction mass was adjusted to 5.0 to 6.0 with hydrochloric acid;
  f) separating out the organic layer;
  g) concentrating the organic layer to obtain a residual solid;
  h) suspending the residual solid in a mixture of water and a ketonic solvent at above 40° C.;
  i) heating the suspension at above 55° C.; and
  j) isolating azilsartan medoxomil crystalline Form H1.

In another aspect, the present invention provides a pharmaceutical composition comprising crystalline Form H1 of azilsartan medoxomil and pharmaceutically acceptable excipients.

In another aspect, the present invention provides a crystalline Form of azilsartan medoxomil designated as Form H2 characterized by peaks in the powder x-ray diffraction spectrum having 2θ angle positions at about 6.9, 12.3, 16.0, 17.0, 22.6 and 23.1±0.2 degrees.

In another aspect, the present invention provides a process for the preparation of azilsartan medoxomil crystalline Form H2, which comprises:
  a) suspending azilsartan medoxomil in an alcoholic solvent;
  b) heating the suspension obtained in step (a) at above 40° C.;
  c) cooling the solution obtained in step (b) at below 20° C.; and
  d) isolating azilsartan medoxomil crystalline Form H2.

In another aspect, the present invention provides a pharmaceutical composition comprising crystalline Form H2 of azilsartan medoxomil and pharmaceutically acceptable excipients.

In another aspect, the present invention provides a crystalline Form of azilsartan medoxomil designated as Form H3 characterized by peaks in the powder x-ray diffraction spectrum having 2θ angle positions at about 8.3, 8.6, 8.8, 9.3, 10.0 and 19.7±0.2 degrees.

In another aspect, the present invention provides a process for the preparation of azilsartan medoxomil crystalline Form H3, which comprises:
  a) suspending azilsartan medoxomil in a ketonic solvent;
  b) heating the suspension obtained in step (a) at above 40° C.;
  c) cooling the solution obtained in step (b) at below −10° C.; and
  d) isolating azilsartan medoxomil crystalline Form H3.

In another aspect, the present invention provides a pharmaceutical composition comprising crystalline Form H3 of azilsartan medoxomil and pharmaceutically acceptable excipients.

In another aspect, the present invention provides an amorphous Form of azilsartan medoxomil potassium.

In another aspect, the present invention provides a process for the preparation of azilsartan medoxomil potassium amorphous Form, which comprises:
  a) providing a solution of azilsartan medoxomil potassium in a solvent and water; and
  b) removing the solvent from the solution to obtain azilsartan medoxomil potassium amorphous Form.

In another aspect, the present invention provides a pharmaceutical composition comprising amorphous Form of azilsartan medoxomil potassium and pharmaceutically acceptable excipients.

Yet in another aspect, the present invention provides a process for the preparation of azilsartan medoxomil potassium crystalline Form II, which comprises:
  a) dissolving azilsartan medoxomil in an ether solvent;
  b) adding potassium 2-ethylhexanoate in an ether solvent to the solution;
  c) maintaining the reaction mass at room temperature; and
  d) isolating azilsartan medoxomil potassium crystalline Form II.

X-ray powder diffraction spectrum was measured on a bruker axs D8 advance X-ray powder diffractometer having a copper-Kα radiation. Approximately 500 gm of sample was gently flattered on a sample holder and scanned from 2 to 50 degrees two-theta, at 0.020 degrees two theta per step and a step time of 1 second. The sample was simply placed on the sample holder. The sample was rotated at 30 rpm at a voltage 40 KV and current 35 mA.

DETAILED DESCRIPTION OF THE INVENTION

The term "room temperature" refers to temperature at about 25 to 35° C.

Figure 1:
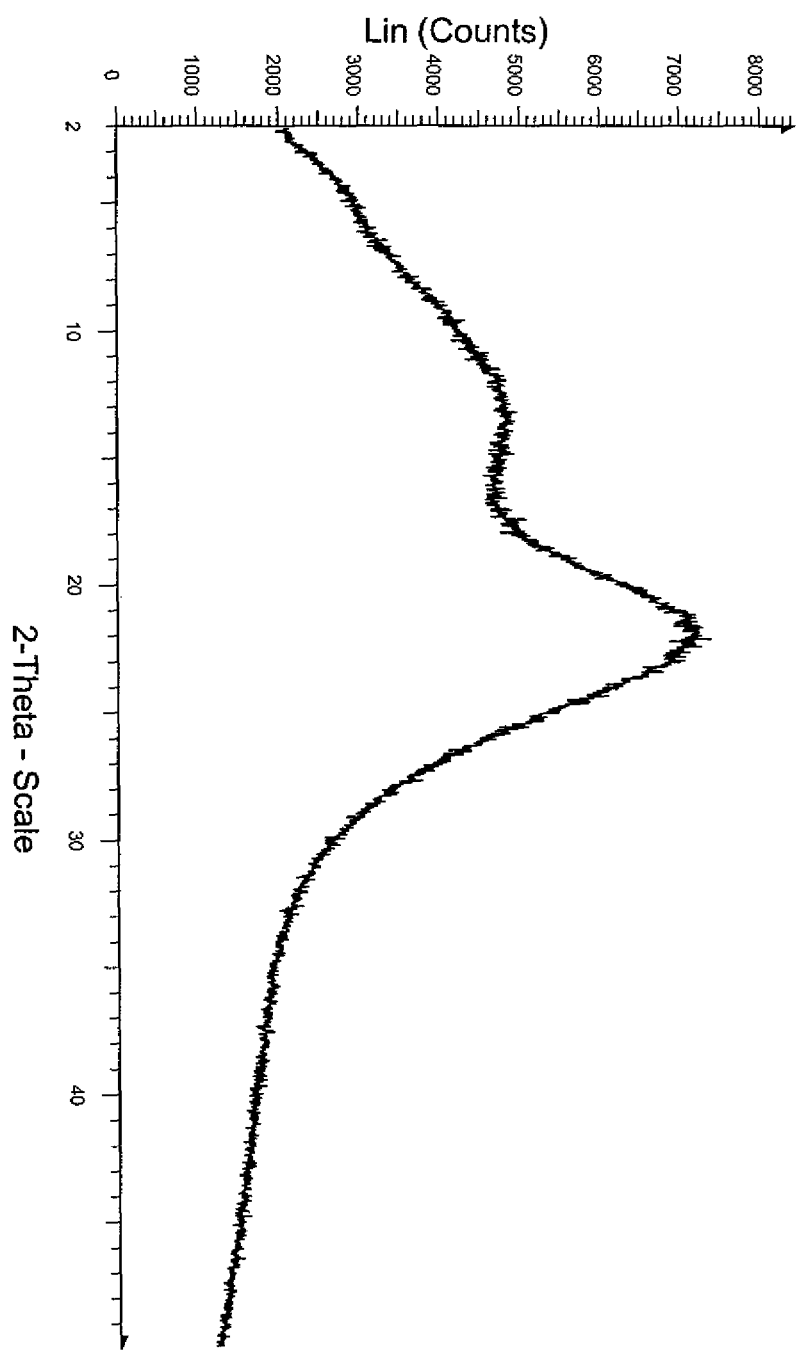
FIG. 1 is an X-ray powder diffraction spectrum of azilsartan acid amorphous Form.
Figure 2:
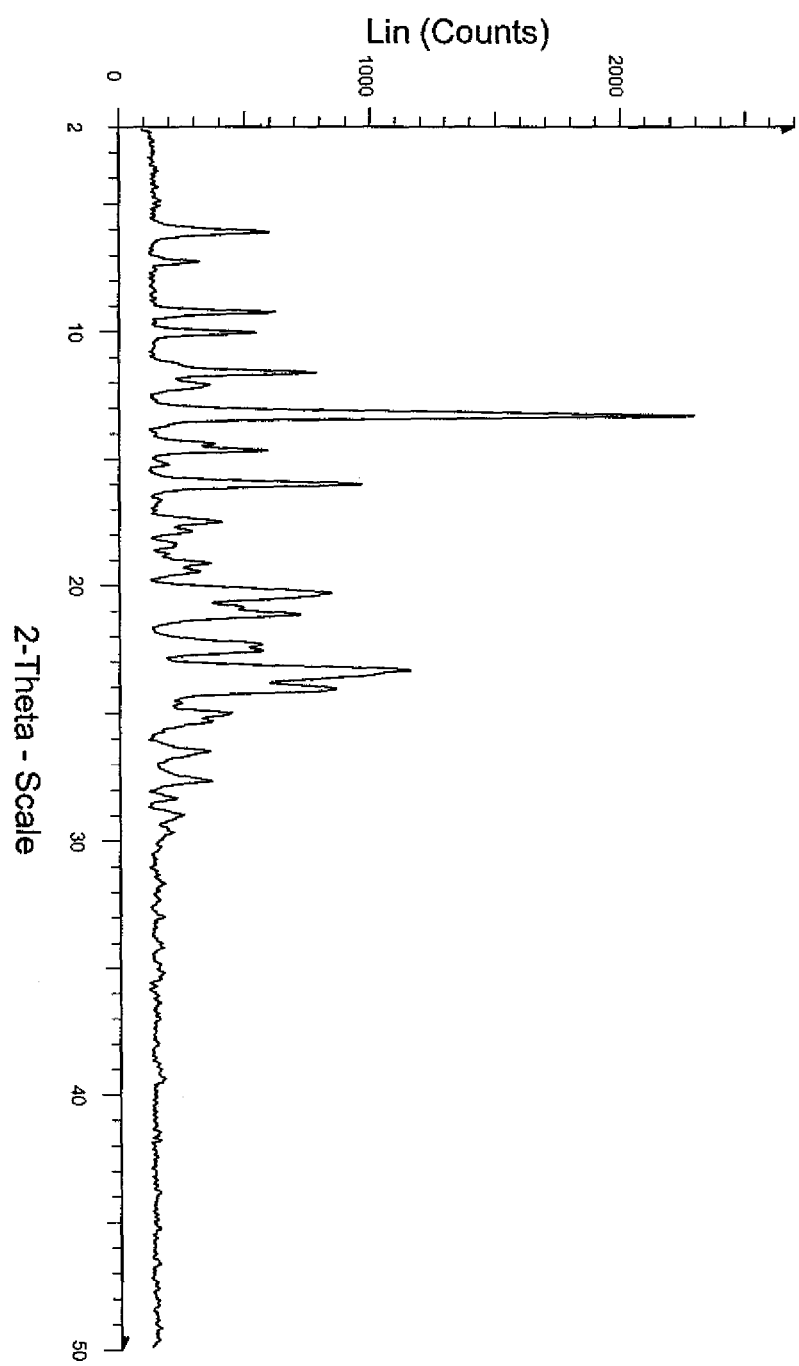
FIG. 2 is an X-ray powder diffraction spectrum of azilsartan medoxomil crystalline Form I.

According to one aspect of the present invention, there is provided an amorphous Form of azilsartan acid. The powdered x-ray diffractogram (PXRD) of azilsartan acid amorphous Form is shown in FIG. 1.

According to another aspect of the present invention, there is provided a process for the preparation of azilsartan acid amorphous Form, which comprises:
 a) providing a solution of azilsartan acid in a solvent; and
 b) removing the solvent from the solution to obtain azilsartan acid amorphous Form.

The solvent used in step (a) may preferably be a solvent or a mixture of solvents selected from methanol, ethanol, isopropyl alcohol, tert-butyl alcohol, n-butanol, isobutyl alcohol, acetone, methyl ethyl ketone, methyl isobutyl ketone, diethyl ketone, methylene chloride, chloroform, carbontetrachloride, ethylene dichloride, ethyl acetate, methyl acetate, isopropyl acetate, tert-butyl methyl acetate, ethyl formate, tetrahydrofuran, 1,4-dioxane, methyl tert-butyl ether and diethyl ether. More preferably the solvents are methanol, acetone, methylene chloride, ethyl acetate, tetrahydrofuran and 1,4-dioxane.

The solvent may be removed from the solution in step (b) by known methods, for example, distillation.

The distillation of the solvent may be carried out at atmospheric pressure or at reduced pressure. The distillation may preferably be carried out until the solvent is almost completely distilled off.

The azilsartan acid amorphous Form of the present invention may also serve as intermediate for preparation of azilsartan medoxomil or salt of azilsartan medoxomil.

According to another aspect of the present invention, there is provided a pharmaceutical composition comprising amorphous Form of azilsartan acid and pharmaceutically acceptable excipients, and optionally other therapeutic ingredients. The amorphous Form may preferably be formulated into tablets, capsules, suspensions, dispersions, injectables or other pharmaceutical forms.

Figure 3:
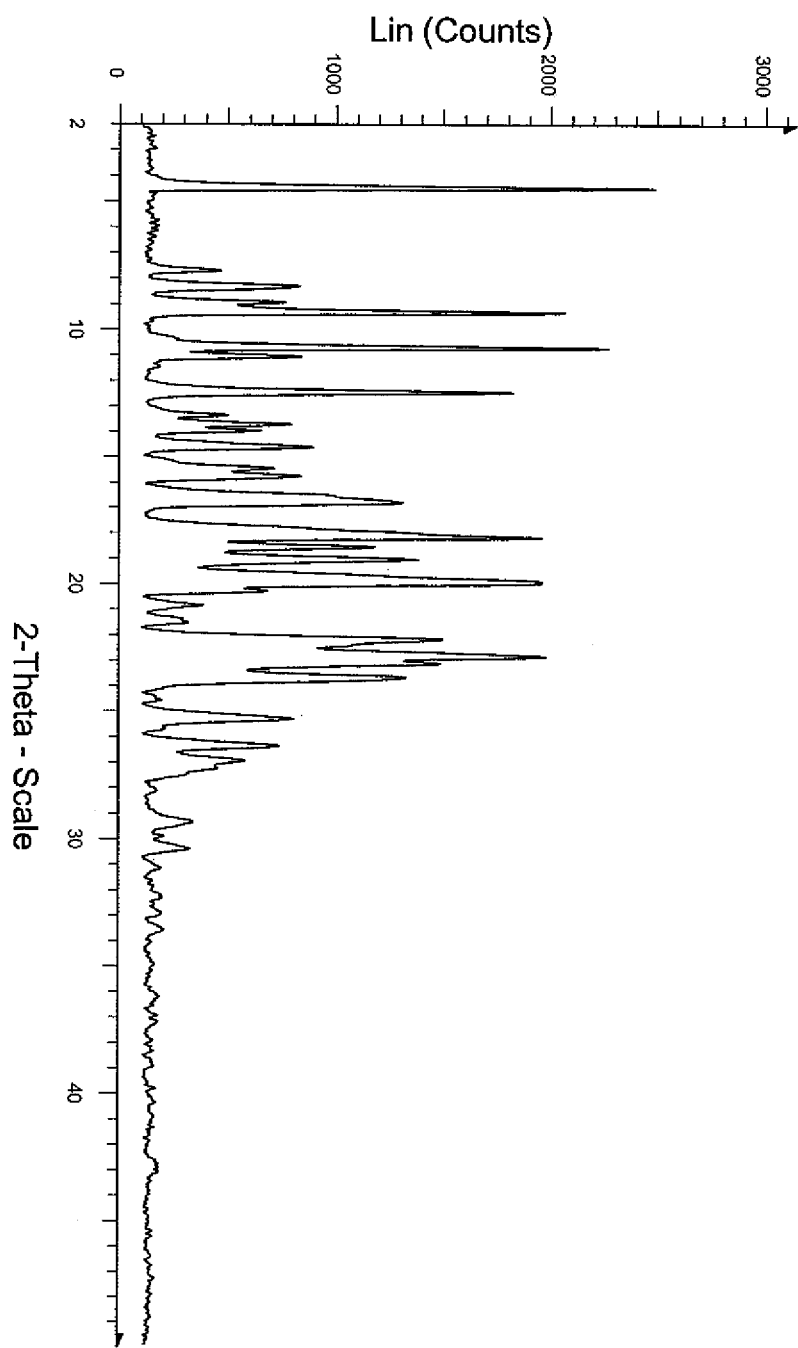
FIG. 3 is an X-ray powder diffraction spectrum of azilsartan medoxomil crystalline Form H1.

According to another aspect of the present invention, there is provided a crystalline Form of azilsartan medoxomil designated as Form H1 characterized by peaks in the powder x-ray diffraction spectrum having 2θ angle positions at about 4.4, 9.3, 10.6, 12.4, 16.8, 17.9, 18.1, 19.0, 19.9, 22.2, 22.8, 23.1 and 23.7±0.2 degrees. The powdered x-ray diffractogram (PXRD) of azilsartan medoxomil crystalline Form H1 is shown in FIG. 3.

According to another aspect of the present invention, there is provided a process for the preparation of azilsartan medoxomil crystalline Form H1, which comprises:
 a) reacting azilsartan acid in dimethylacetamide with 4-hydroxymethyl-5-methtyl-1,3-dioxol-2-one at below 5° C.;
 b) adding p-toluenesulfonyl chloride, N,N-dimethylaminopyridine and potassium carbonate to the reaction mass obtained in step (a) at below 5° C.;
 c) removing the solvent to obtain a residual mass;
 d) adding an ester solvent and water to the residual mass;
 e) pH of the reaction mass was adjusted to 5.0 to 6.0 with hydrochloric acid;
 f) separating out the organic layer;
 g) concentrating the organic layer to obtain a residual solid;
 h) suspending the residual solid in a mixture of water and a ketonic solvent at above 40° C.;
 i) heating the suspension at above 55° C.; and
 j) isolating azilsartan medoxomil crystalline Form H1.

The reaction in step (a) and step (b) may be carried out at about −5 to 0° C.

The solvent may be removed from the solution in step (c) by known methods, for example, distillation.

The distillation of the solvent may be carried out at atmospheric pressure or at reduced pressure. The distillation may preferably be carried out until the solvent is almost completely distilled off.

The ester solvent used in step (d) may preferably be a solvent or a mixture of solvents selected from ethyl acetate, methyl acetate, isopropyl acetate, tert-butyl methyl acetate and ethyl formate. More preferably the ester solvent is ethyl acetate.

Preferably the organic layer is concentrated in step (g) by distilling off the solvent. The distilling off the solvent may be carried out at atmospheric pressure or at reduced pressure. The distillation may preferably be carried out until the solvent is almost completely distilled off.

The ketonic solvent used in step (h) may preferably be a solvent or a mixture of solvents selected from acetone, methyl ethyl ketone, diethyl ketone and methyl isobutyl ketone. More preferably the ketonic solvent is acetone.

The reaction in step (h) may be carried out at about 45 to 50° C.

The reaction in step (i) may be heated to 60 to 70° C.

The azilsartan medoxomil crystalline Form H1 may be isolated in step (j) by methods known such as filtration or centrifugation.

According to another aspect of the present invention, there is provided a pharmaceutical composition comprising crystalline Form H1 of azilsartan medoxomil and pharmaceutically acceptable excipients, and optionally other therapeutic ingredients. The crystalline Form H1 may preferably be formulated into tablets, capsules, suspensions, dispersions, injectables or other pharmaceutical forms.

Figure 4:
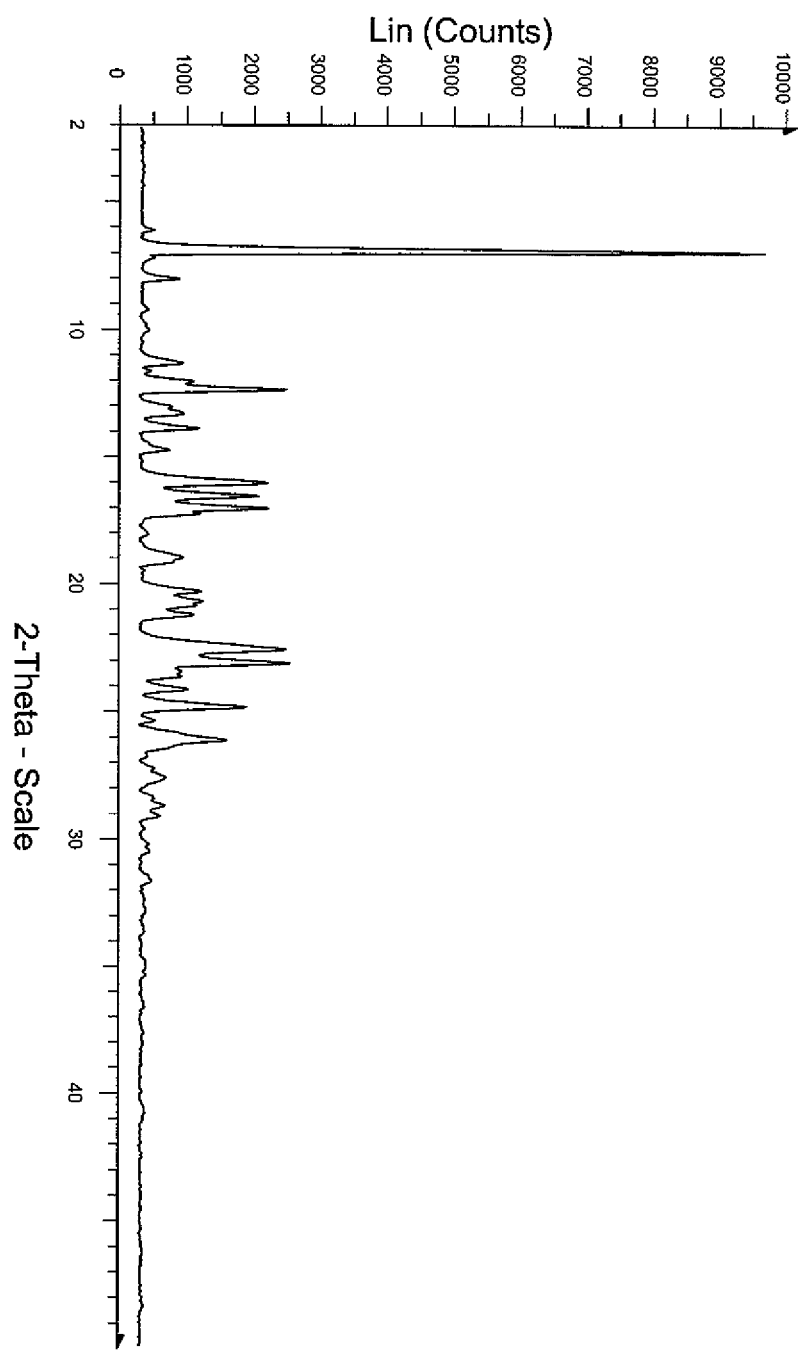
FIG. 4 is an X-ray powder diffraction spectrum of azilsartan medoxomil crystalline Form H2.

According to another aspect of the present invention, there is provided a crystalline Form of azilsartan medoxomil designated as Form H2 characterized by peaks in the powder x-ray diffraction spectrum having 2θ angle positions at about 6.9, 12.3, 16.0, 17.0, 22.6 and 23.1±0.2 degrees. The powdered x-ray diffractogram (PXRD) of azilsartan medoxomil crystalline Form H2 is shown in FIG. 4.

According to another aspect of the present invention, there is provided a process for the preparation of azilsartan medoxomil crystalline Form H2, which comprises:
 a) suspending azilsartan medoxomil in an alcoholic solvent;
 b) heating the suspension obtained in step (a) at above 40° C.;
 c) cooling the solution obtained in step (b) at below 20° C.; and
 d) isolating azilsartan medoxomil crystalline Form H2.

The alcoholic solvent used in step (a) may preferably be a solvent or a mixture of solvents selected from methanol, ethanol, isopropyl alcohol and n-butanol, and more preferably the alcoholic solvent is methanol.

The reaction in step (b) may be heated to at about 65 to 75° C.

The reaction in step (c) may be cooled to at about −5 to 5° C.

The azilsartan medoxomil crystalline Form H2 may be isolated in step (d) by methods known such as filtration or centrifugation.

According to another aspect of the present invention, there is provided a pharmaceutical composition comprising crystalline Form H2 of azilsartan medoxomil and pharmaceutically acceptable excipients, and optionally other therapeutic ingredients. The crystalline Form H2 may preferably be formulated into tablets, capsules, suspensions, dispersions, injectables or other pharmaceutical forms.

Figure 5:
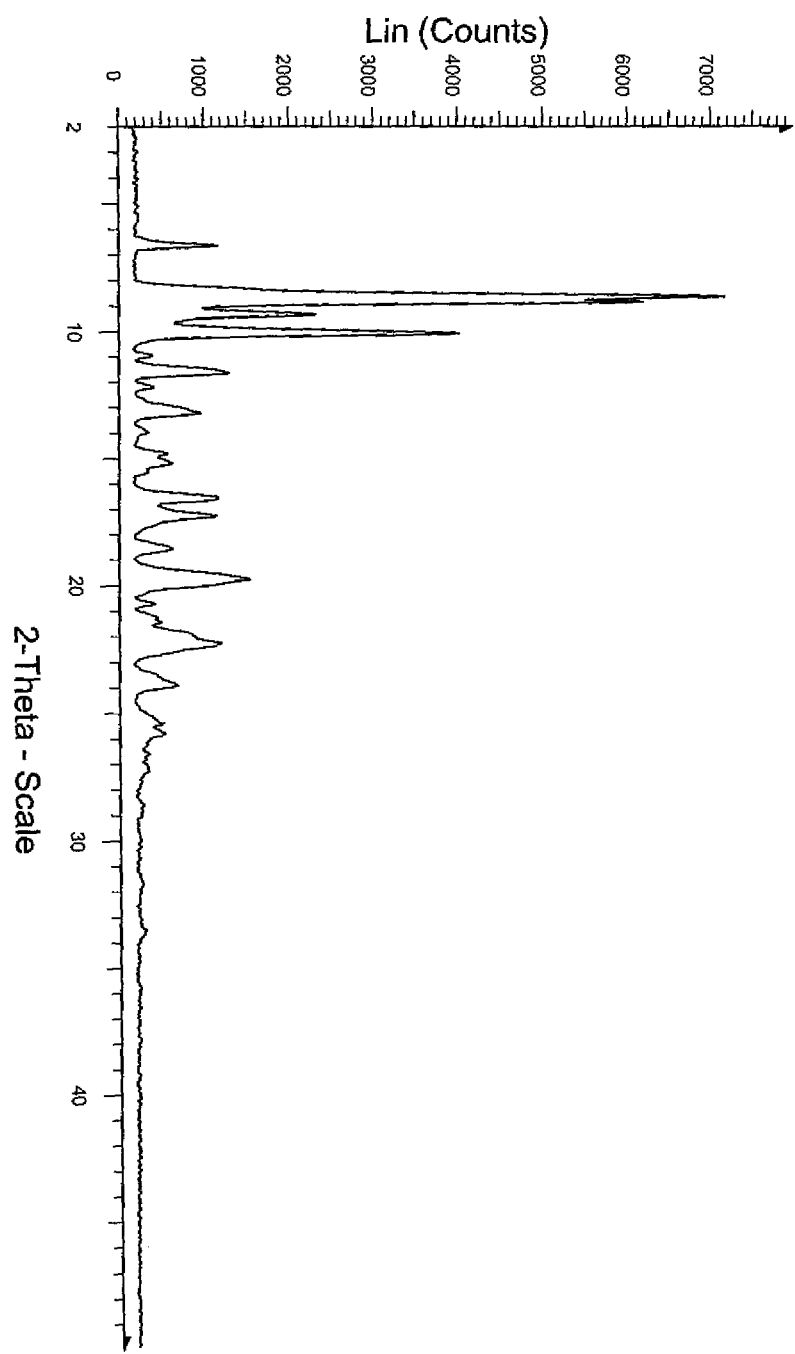
FIG. 5 is an X-ray powder diffraction spectrum of azilsartan medoxomil crystalline Form H3.

According to another aspect of the present invention, there is provided a crystalline Form of azilsartan medoxomil designated as Form H3 characterized by peaks in the powder x-ray diffraction spectrum having 2θ angle positions at about 8.3, 8.6, 8.8, 9.3, 10.0 and 19.7±0.2 degrees. The powdered x-ray diffractogram (PXRD) of azilsartan medoxomil crystalline Form H3 is shown in FIG. 5.

According to another aspect of the present invention, there is provided a process for the preparation of azilsartan medoxomil crystalline Form H3, which comprises:
 a) suspending azilsartan medoxomil in a ketonic solvent;
 b) heating the suspension obtained in step (a) at above 40° C.;
 c) cooling the solution obtained in step (b) at below −10° C.; and
 d) isolating azilsartan medoxomil crystalline Form H3.

The ketonic solvent used in step (a) may preferably be a solvent or a mixture of solvents selected from acetone, methyl ethyl ketone, methyl isobutyl ketone and diethyl ketone, and more preferably the ketonic solvent is acetone.

The step (b) may preferably be carried out at about 45 to 65° C.

The step (c) may preferably be carried out at about −25 to −35° C.

The azilsartan medoxomil crystalline Form H3 may be isolated in step (d) by methods known such as filtration or centrifugation.

According to another aspect of the present invention, there is provided a pharmaceutical composition comprising crystalline Form H3 of azilsartan medoxomil and pharmaceutically acceptable excipients, and optionally other therapeutic ingredients. The crystalline Form H3 may preferably be formulated into tablets, capsules, suspensions, dispersions, injectables or other pharmaceutical forms.

The azilsartan medoxomil crystalline Form H1, Form H2 and Form H3 of the present invention may also serve as intermediate for preparation of salt of azilsartan medoxomil.

Figure 6:
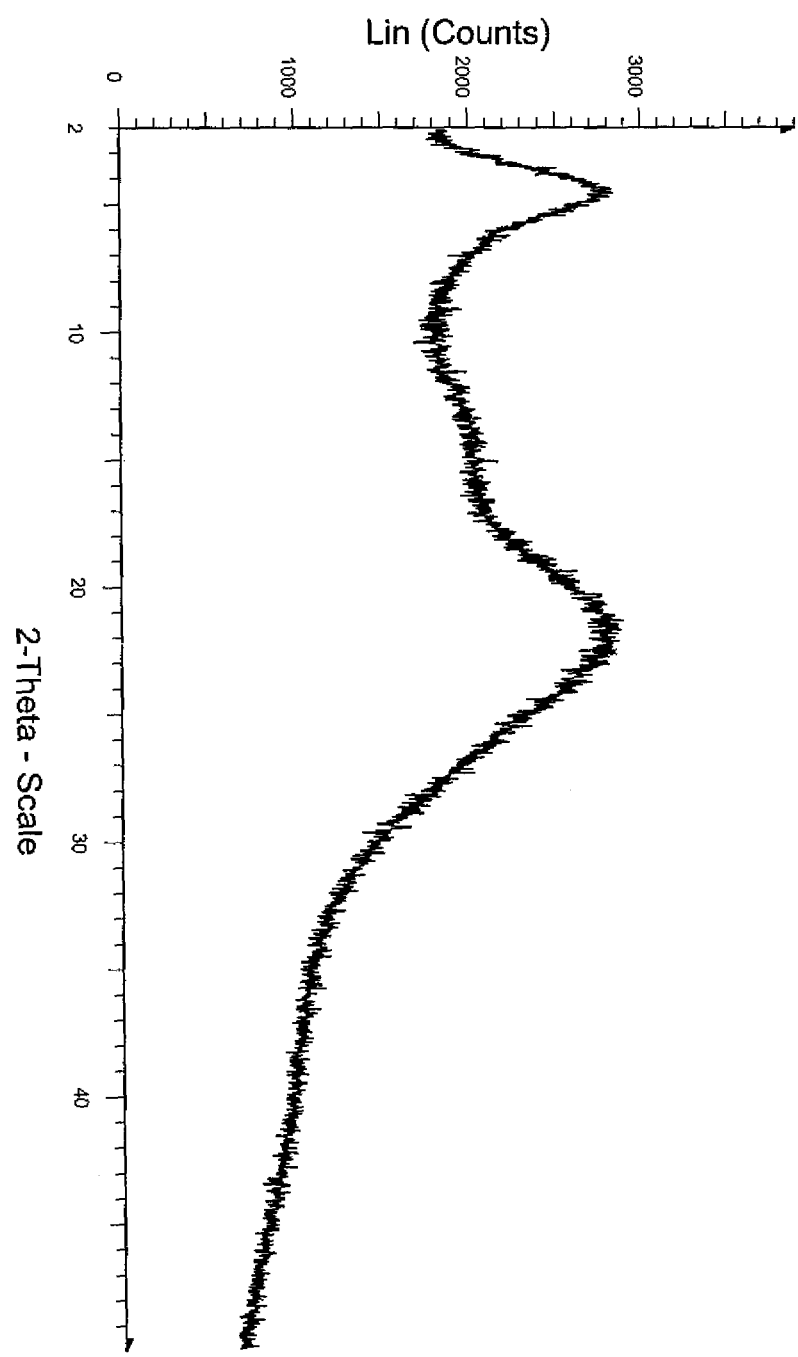
FIG. 6 is an X-ray powder diffraction spectrum of azilsartan medoxomil potassium amorphous Form.

According to another aspect of the present invention, there is provided an amorphous Form of azilsartan medoxomil potassium. The powdered x-ray diffractogram (PXRD) of azilsartan medoxomil potassium amorphous Form is shown in FIG. 6.

According to another aspect of the present invention, there is provided a process for the preparation of azilsartan medoxomil potassium amorphous Form, which comprises:
 a) providing a solution of azilsartan medoxomil potassium in a solvent and water; and
 b) removing the solvent from the solution to obtain azilsartan medoxomil potassium amorphous Form.

The solvent used in step (a) may preferably be a solvent or a mixture of solvents selected from methanol, ethanol, isopropyl alcohol, tert-butyl alcohol, n-butanol, isobutyl alcohol, acetone, methyl ethyl ketone, methyl isobutyl ketone, diethyl ketone, methylene chloride, chloroform, carbontetrachloride, ethylene dichloride, ethyl acetate, methyl acetate, isopropyl acetate, tert-butyl methyl acetate, ethyl formate, tetrahydrofuran, 1,4-dioxane, methyl tert-butyl ether, diethyl ether, acetonitrile, propionitrile, butyronitrile and benzonitrile. More preferably the solvents are tetrahydrofuran, methylene chloride, 1,4-dioxane and acetonitrile.

The solvent may be removed from the solution in step (b) by known methods, for example, distillation.

The distillation of the solvent may be carried out at atmospheric pressure or at reduced pressure. The distillation may preferably be carried out until the solvent is almost completely distilled off.

According to another aspect of the present invention, there is provided a pharmaceutical composition comprising amorphous Form of azilsartan medoxomil potassium and pharmaceutically acceptable excipients, and optionally other therapeutic ingredients. The amorphous Form may preferably be formulated into tablets, capsules, suspensions, dispersions, injectables or other pharmaceutical forms.

According to another aspect of the present invention, there is provided a process for the preparation of azilsartan medoxomil potassium crystalline Form II, which comprises:
 a) dissolving azilsartan medoxomil in an ether solvent;
 b) adding potassium 2-ethylhexanoate in an ether solvent to the solution;
 c) maintaining the reaction mass at room temperature; and
 d) isolating azilsartan medoxomil potassium crystalline Form II.

The ether solvent used in step (a) and step (b) may preferably be a solvent or a mixture of solvents selected from teterahydrofuran, 1,4-dioxane, tert-butyl methyl ether and diethyl ether, and more preferably the ether solvent is teterahydrofuran.

The azilsartan medoxomil potassium crystalline Form II may be isolated in step (d) by known methods such as filtration or centrifugation.

The contents of azilsartan acid, azilsartan medoxomil and azilsartan medoxomil potassium are determined by High performance liquid chromatography (HPLC).

The invention will now be further described by the following examples, which are illustrative rather than limiting.

REFERENCE EXAMPLES

Reference Example 1

Preparation of Azilsartan Medoxomil Crystalline Form I

To a mixture of 2-Ethoxy-1-{[2'-(5-oxo-4,5-dihydro-1,2,4-oxadiazol-3-yl)biphenyl-4-yl]methyl}-1H-benzimidazole-7-carboxylic acid (5 gm) and N,N-dimethylacetamide (50 ml) were added to p-toluenesulfonyl chloride (3.5 gm), potassium carbonate (4 gm), N,N-dimethylaminopyridine (0.5 gm) and 4-hydroxymethyl-5-methyl-1,3-dioxol-2-one (3.5 gm) at 0 to 5° C. The reaction mass was maintained for 2 hours at 0 to 5° C. and filtered through hi-flow bed. The pH of the filtrate thus obtained was adjusted to 2.0 with acetic acid and then added water (150 ml). The reaction mass was stirred for 30 minutes and filtered to provide a wet solid. To the wet solid was added acetone (15 ml) and water (35 ml) and maintained for 2 hours at room temperature. The contents were then cooled to 0 to 5° C. and maintained for 2 hours. The separated solid was filtered and then dried to provide 3 gm of azilsartan medoxomil crystalline Form I.

EXAMPLES

Example 1

Preparation of Azilsartan Acid Amorphous Form

Azilsartan acid (10 gm) was dissolved in methylene chloride (300 ml) and then added methanol (100 ml) to provide a clear solution. The solution was stirred for 10 minutes at room temperature and filtered through hi-flow bed. The solvent was distilled off under vacuum at below 55° C. to obtain 6.5 gm of azilsartan acid amorphous Form.

Example 2

Preparation of Azilsartan Acid Amorphous Form

Example 1 was repeated using teterahydrofuran solvent instead of methylene chloride solvent to provide azilsartan acid amorphous Form.

Example 3

Preparation of Azilsartan Acid Amorphous Form

Example 1 was repeated using ethyl acetate solvent instead of methylene chloride solvent to provide azilsartan acid amorphous Form.

Example 4

Preparation of Azilsartan Acid Amorphous Form

Example 1 was repeated using 1,4-dioxane solvent instead of methylene chloride solvent to provide azilsartan acid amorphous Form.

Example 5

Preparation of Azilsartan Acid Amorphous Form

Example 1 was repeated using acetone solvent instead of methylene chloride solvent to provide azilsartan acid amorphous Form.

Example 6

Preparation of Azilsartan Medoxomil Crystalline Form H1

To a mixture of 2-Ethoxy-1-{[2'-(5-oxo-4,5-dihydro-1,2,4-oxadiazol-3-yl)biphenyl-4-yl]methyl}-1H-benzimidazole-7-carboxylic acid (200 gm) and N,N-dimethylacetamide (2000 ml) were added to p-toluenesulfonyl chloride (140 gm), potassium carbonate (159 gm), N,N-dimethylaminopyridine (20 gm) and 4-hydroxymethyl-5-methyl-1,3-dioxol-2-one (140 gm) at 0 to 5° C. The reaction mass was maintained for 2 hours at 0 to 5° C. and filtered through hi-flow bed. The solvent was distilled off under vacuum below 75° C. to obtain a residual mass. To the residual mass was added ethyl acetate (2000 ml) and water (2000 ml) and pH was adjusted to 5.4 with hydrochloric acid (1N). The layers were separated and aqueous layer was extracted with ethyl acetate. Combined organic layers were dried with sodium sulfate and then concentrated to provide a residual solid. To the residual solid was added acetone (600 ml) and water (1400 ml) at 45° C. and then heated to 65° C. for 30 minutes. The contents were then cooled to room temperature and maintained for 1 hour 30 minutes. The separated solid was filtered and then dried to provide 202 gm of azilsartan medoxomil crystalline Form H1.

Example 7

Preparation of Azilsartan Medoxomil Crystalline Form H1

Example 6 was repeated using methyl ethyl ketone solvent instead of acetone solvent to provide azilsartan medoxomil crystalline Form H2.

Example 8

Preparation of Azilsartan Medoxomil Crystalline Form H2

Azilsartan medoxomil (250 gm) was dissolved in methanol (1400 ml) and then heated to 65° C. to provide a clear solution. The solution was then cooled to room temperature and stirred for 1 hour. The contents were then further cooled to 0° C. and maintained for 30 minutes. The separated solid was filtered and then dried to provide 208 gm of azilsartan medoxomil crystalline Form H2.

Example 9

Preparation of Azilsartan Medoxomil Crystalline Form H2

Example 8 was repeated using ethanol solvent instead of methanol solvent to provide azilsartan medoxomil crystalline Form H2.

Example 10

Preparation of Azilsartan Medoxomil Crystalline Form H2

Example 8 was repeated using isopropanol solvent instead of methanol solvent to provide azilsartan medoxomil crystalline Form H2.

Example 11

Preparation of Azilsartan Medoxomil Crystalline Form H3

Azilsartan medoxomil (20 gm) was dissolved in acetone (400 ml) and then heated to 50° C. The contents were stirred for 20 minutes at 50° C. and filtered through hi-flow bed. The filtrate thus obtained was then cooled to −30 to −35° C. and stirred for 1 hour. The separated solid was filtered and then dried to provide 15 gm of azilsartan medoxomil crystalline Form H3.

Example 12

Preparation of Azilsartan Medoxomil Crystalline Form H3

Example 11 was repeated using methyl ethyl ketone instead of acetone to provide azilsartan medoxomil crystalline Form H3.

Example 13

Preparation of Azilsartan Medoxomil Crystalline Form H3

Example 11 was repeated using diethyl ketone instead of acetone to provide azilsartan medoxomil crystalline Form H3.

Example 14

Preparation of Azilsartan Medoxomil Amorphous Form

Azilsartan medoxomil (10 gm) was dissolved in tetrahydrofuran (250 ml) under stirring at room temperature to provide a clear solution. The solution was filtered through celite bed and the solvent was distilled off under vacuum to provide 9 gm of azilsartan medoxomil amorphous Form.

Example 15

Preparation of Azilsartan Medoxomil Potassium Amorphous Form

Azilsartan medoxomil potassium (11 gm) was added to a mixture of teterahydrofuran (450 ml) and water (40 ml) at 0 to 5° C. for 15 minutes. The solution was filtered through hi-flow bed and the solvent was distilled off under vacuum to provide a solid. The solid thus obtained was then dried to provide 6 gm of azilsartan medoxomil potassium amorphous Form.

Example 16

Preparation of Azilsartan Medoxomil Potassium Amorphous Form

Azilsartan medoxomil potassium (20 gm) was added to a mixture of acetonitrile (160 ml) and water (20 ml) at 0 to 5° C. for 15 minutes. The solution was filtered through hi-flow bed. The resulting filtrate was subjected to lyophilized at room temperature for 24 hours to obtain 15 gm of azilsartan medoxomil potassium amorphous Form.

Example 17

Preparation of Azilsartan Medoxomil Potassium Crystalline Form II

Azilsartan medoxomil (6 gm) was dissolved in teterahydrofuran (120 ml) under stirring at room temperature to provide a clear solution. The solution was filtered through celite bed and then cooled to 0° C. To the filtrate was added a solution of potassium 2-ethylhexanoate (1.8 gm) in tetrahydrofuran (10 ml) slowly for 20 minutes at 0° C. and temperature of the reaction mass was raised to room temperature. The separated solid was filtered and then dried to provide 4.5 gm of azilsartan medoxomil potassium crystalline Form II.

We claim:

1. Amorphous Form of azilsartan acid, characterized by an X-ray powder diffractogram as shown in FIG. 1.

2. A process for the preparation of amorphous Form of azilsartan acid as claimed in claim 1, which comprises:
   a. providing a solution of azilsartan acid in a solvent; and
   b. removing the solvent from the solution to obtain azilsartan acid amorphous Form.

3. The process according to claim 2, wherein the solvent used in step (a) is a solvent or a mixture of solvents selected from the group consisting of methanol, ethanol, isopropyl alcohol, tert-butyl alcohol, n-butanol, isobutyl alcohol, acetone, methyl ethyl ketone, methyl isobutyl ketone, diethyl ketone, methylene chloride, chloroform, carbontetrachloride, ethylene dichloride, ethyl acetate, methyl acetate, isopropyl acetate, tert-butyl methyl acetate, ethyl formate, tetrahydrofuran, 1,4-dioxane, methyl tert-butyl ether and diethyl ether.

4. Azilsartan medoxomil crystalline Form H1, characterized by peaks in the powder x-ray diffraction spectrum having 2θ angle positions at about 4.4, 9.3, 10.6,12.4, 16.8,17.9,18.1,19.0,19.9,22.2,22.8,23.1 and 23.7±0.2 degrees, or characterized by an x-ray powder diffractogram as shown in FIG. 3.

5. A process for the preparation of azilsartan medoxomil crystalline Form H1 as claimed in claim 4, which comprises:
   a. reacting azilsartan acid in dimethylacetamide with 4-hydroxymethyl-5-methyl -1,3-dioxol-2-one at below 5° C.;
   b. adding p-toluenesulfonyl chloride, N,N-dimethylaminopyridine and potassium carbonate to the reaction mass obtained in step (a) at below 5° C.;
   c. removing the solvent to obtain a residual mass;
   d. adding an ester solvent and water to the residual mass;
   e. adjusting the pH of the reaction mass to 5.0 to 6.0 with hydrochloric acid;
   f. separating out the organic layer;
   g. concentrating the organic layer to obtain a residual solid;
   h. suspending the residual solid in a mixture of water and a ketonic solvent at above 40° C.;
   i. heating the suspension at above 55° C.; and
   j. isolating azilsartan medoxomil crystalline Form H1.

6. The process according to claim 5, wherein the reaction temperature in step (a) and step (b) is at about −5 to 0° C.; in step (h) is at about 45 to 50° C.; in step (i) is at about 60 to 70° C.

7. The process according to claim 5, wherein the ester solvent used in step (d) is a solvent or a mixture of solvents selected from ethyl acetate, methyl acetate, isopropyl acetate, tert-butyl methyl acetate and ethyl formate; step (h) is a solvent or a mixture of solvents selected from acetone, methyl ethyl ketone, diethyl ketone and methyl isobutyl ketone.

8. Azilsartan medoxomil crystalline Form H2, characterized by peaks in the powder x-ray diffraction spectrum having 2θ angle positions at about 6.9,12.3,16.0,17.0, 22.6 and 23.1±0.2 degrees, or characterized by an x-ray powder diffractogram as shown in FIG. 4.

9. A process for the preparation of azilsartan medoxomil crystalline Form H2 as claimed in claim 8, which comprises:
   a. suspending azilsartan medoxomil in an alcoholic solvent;
   b. heating the suspension obtained in step (a) at above 40° C.;
   c. cooling the solution obtained in step (b) at below 20° C.; and
   d. isolating azilsartan medoxomil crystalline Form H2.

10. The process according to claim 9, wherein the alcoholic solvent in step (a) is a solvent or a mixture of solvents selected from methanol, ethanol, isopropyl alcohol and n-butanol.

11. Azilsartan medoxomil crystalline Form H3, characterized by peaks in the powder x-ray diffraction spectrum having 2θ angle positions at about 8.3, 8.6, 8.8, 9.3, 10.0 and 19.7±0.2 degrees, or characterized by an x-ray powder diffractogram as shown in FIG. 5.

12. A process for the preparation of azilsartan medoxomil crystalline Form H3 as claimed in claim 11, which comprises:
   a. suspending azilsartan medoxomil in a ketonic solvent;
   b. heating the suspension obtained in step (a) at above 40° C.;
   c. cooling the solution obtained in step (b) at below −10° C.; and
   d. isolating azilsartan medoxomil crystalline Form H3.

13. The process according to claim 12, wherein the ketonic solvent used in step (a) is a solvent or a mixture of solvents selected from acetone, methyl ethyl ketone, methyl isobutyl ketone and diethyl ketone.

14. Azilsartan medoxomil potassium amorphous Form, characterized by an x-ray powder diffractogram as shown in FIG. 6.

15. A process for the preparation of azilsartan medoxomil potassium amorphous Form as claimed in claim 14, which comprises:

a. providing a solution of azilsartan medoxomil potassium in a solvent and water; and
b. removing the solvent from the solution to obtain azilsartan medoxomil potassium amorphous Form.

16. The process according to claim 15, wherein the solvent in step (a) is a solvent or a mixture of solvents selected from methanol, ethanol, isopropyl alcohol, tert-butyl alcohol, n-butanol, isobutyl alcohol, acetone, methyl ethyl ketone, methyl isobutyl ketone, diethyl ketone, methylene chloride, chloroform, carbontetrachloride, ethylene dichloride, ethyl acetate, methyl acetate, isopropyl acetate, tert-butyl methyl acetate, ethyl formate, tetrahydrofuran, 1,4-dioxane, methyl tert-butyl ether, diethyl ether, acetonitrile, propionitrile, butyronitrile and benzonitrile.

17. A pharmaceutical composition of amorphous Form of azilsartan acid as claimed in claim 1 and pharmaceutically acceptable excipients, and optionally other therapeutic ingredients.

18. A pharmaceutical composition of crystalline Form H1 of azilsartan medoxomil as claimed in claim 4 and pharmaceutically acceptable excipients, and optionally other therapeutic ingredients.

19. A pharmaceutical composition of crystalline Form H2 of azilsartan medoxomil as claimed in claim 8 and pharmaceutically acceptable excipients, and optionally other therapeutic ingredients.

20. A pharmaceutical composition of crystalline Form H3 of azilsartan medoxomil as claimed in claim 11 and pharmaceutically acceptable excipients, and optionally other therapeutic ingredients.

21. A pharmaceutical composition of amorphous Form of azilsartan medoxomil potassium as claimed in claim 14 and pharmaceutically acceptable excipients, and optionally other therapeutic ingredients.

* * * * *